United States Patent [19]

Lynch et al.

[11] Patent Number: 5,950,633
[45] Date of Patent: Sep. 14, 1999

[54] MICROSURGICAL TECHNIQUE FOR COSMETIC SURGERY

[75] Inventors: Richard J. Lynch, Middlebury, Conn.;
Tommy L. Turpin, Cordova, Tenn.

[73] Assignee: Ethicon, Inc., Somerville, N.J.

[21] Appl. No.: 08/942,926

[22] Filed: Oct. 2, 1997

[51] Int. Cl.$^6$ .................................................. A61B 19/00
[52] U.S. Cl. ............................ 128/898; 623/16; 606/53;
606/60; 606/73; 606/139
[58] Field of Search ................................... 128/897, 898;
606/213, 53, 60, 72, 73, 104, 139; 623/11,
16, 66

[56] References Cited

U.S. PATENT DOCUMENTS 5,611,815   3/1997   Lorenc ..................................... 606/213

OTHER PUBLICATIONS

Brewer, Keith, F., M.D., "Endoscopic Brow Lifts", Association of Plastic Surgery Assistants Network Publication, vol. 12, No. 1, pp. 13–15 (Spring 1997).
Barroso, Eduardo, M.D. and Mustoe, Thomas, M.D., "Surgical Technique: Endoscopic Browlift with Rigid Fixation Using the Mitek 2.0 mm Tacit™ Threaded Anchor", Mitek® Products Ethicon a Johnson & Johnson Company, 60 Glacier Drive, Westwood, MA 02090 (P/N 900196 Rev. A Jan. 1997. Plastic Surgery Conference Series, "Application of Tacit Anchors in Endoscopic Brow Lifts", Baptist Health Systems of South Florida, Speaker: Eduardo Barroso, M.D., Mar. 13, 1997.

"The Mitek® 2.0 mm Tacit™ Threaded Anchor", Mitek Products Ethicon a Johnson & Johnson Company, Mitek Surgical Products, Inc., 60 Glacier Drive, Westwood, MA 02090 (P/N 900188 Rev. B Nov. 1996).

*Primary Examiner*—Mickey Yu
*Assistant Examiner*—Dinh X. Nguyen
*Attorney, Agent, or Firm*—Nutter, McClennen & Fish, LLP

[57] ABSTRACT

A procedure for supporting the soft tissue of a patient's scalp in a superior position using a microanchor includes forming a plurality of incisions proximate to the soft tissue to be moved, inserting an endoscope through at least of one of the incisions and undermining the soft tissue to be moved while at least a portion of the undermining process is viewed through the endoscope. At least one microanchor having a generally cylindrical body including a first bone contacting end, a second trailing end and bone fixation means formed on at least a portion of an outer surface of the microanchor between the first and second ends is provided. Each of the one or more microanchors has a length of less than about 4.0 mm and has a predetermined length of suture thread attached thereto. At least one pilot hole is formed in the patient's cranium through the incisions made therein. The one or more microanchors are inserted into the one or more pilot holes, the soft tissue is moved to the desired superior position and the soft tissue is sutured into that position using the suture thread attached to the microanchor.

16 Claims, 6 Drawing Sheets

FIG. 13

MICROSURGICAL TECHNIQUE FOR COSMETIC SURGERY

CROSS-REFERENCE TO RELATED APPLICATION

Not Applicable.

STATEMENT REGARDING FEDERALLY SPONSORED RESEARCH

Not Applicable.

FIELD OF THE INVENTION

The present invention relates to a technique for performing plastic or cosmetic surgery using microanchors.

BACKGROUND OF THE INVENTION

The brow lift is a basic procedure for rejuvenating the upper portion of a patient's face. The brow lift procedure may be used to elevate the eye brows, remove or lessen forehead wrinkles, reduce frown lines, smooth the nasion and elevate the nasal tip. These results are generally achieved by elevating the top of the patient's brow from the skull and suspending the brow in a superior position for a sufficient period of time so that the soft and connective tissues of the patient's scalp knit in place, leaving the patient with the desired effects.

In the past, surgeons performed invasive surgery using standard surgical tools at open surgical sites, typically performing a bicoronal incision with subgaleal dissection, to complete a brow lift procedure. These techniques were very limited in their application and resulted in significant scarring to the patient.

More recently, surgeons have begun to use endoscopic techniques to perform brow lift procedures. Endoscopic procedures allow the surgeon to make a small incision or incisions, extend surgical tools through the small incisions and perform the procedure while viewing the surgical site with an endoscope. In this manner, the brow lift procedure is performed without the need for large surgical incisions that are required in open surgical techniques.

Once the surgeon has moved the brow to a superior position, the soft tissue must be suspended in that position for a sufficient time to allow healing to occur. External means, such as screws and staples, have been used to suspend the soft tissue in place. These devices may leave the patient susceptible to infections, require a great deal of bandaging and leave extensive scars. More recently, internal means, such as surgical pins or posts, have been applied. These devices work for their intended purposes, but they require the surgeon to reopen the skin to remove them and they can create an internal space which is susceptible to undesirable effects such as fluid collection.

Additionally, tissue fixation methods that do not a require reopening of the patient's skin to remove fixation devices have been attempted, including bone tunneling and deployment of resorbable fixation devices. Bone tunneling involves drilling two interconnecting holes into the patient's cranium and leaving a "bridge" between the holes. A suture thread may then be routed though this tunnel and used to fix the patient's scalp tissue in place. Despite the strength of cranial bone, this method can be difficult to perform without weakening or breaking the bone "bridge" that fixes the suture thread to the cranium. Resorbable fixation devices also have drawbacks, including the inability to adjust the timing of the fixation device's release after implantation in response to individual healing rates and the creation of internal spaces as with surgical pins or posts.

SUMMARY OF THE INVENTION

The present invention provides a procedure for supporting the soft tissue of a patient's scalp in a superior position using a device, such as a microanchor, for anchoring sutures to bone. The procedure includes forming a plurality of incisions proximate to the soft tissue to be moved. An endoscope is then inserted through at least of one of the incisions and the soft tissue to be moved is undermined while at least a portion of the undermining process is viewed through the endoscope.

At least one suture anchor device having a generally cylindrical body including a first bone contacting end, a second trailing end and bone fixation element formed on at least a portion of an outer surface of the suture anchor between the first and second ends is provided. Each of the one or more suture anchor devices has a length of less than about 4.0 mm and has a predetermined length of suture thread attached thereto.

At least one pilot hole is formed in the patient's cranium through the incisions made therein. The one or more suture anchor devices are inserted into the one or more pilot holes, the soft tissue is moved to the desired superior position and the soft tissue is sutured into that position using the suture thread attached to the anchor device.

In one embodiment, the suture anchor device is a threaded microanchor having a length of less than about 4.0 mm and a major diameter of less than about 2.4 mm. Preferably, the threaded microanchor has a length of about 3.5 mm and a major diameter of about 2.0 mm.

In an additional embodiment, the suture anchor device is a non-threaded microanchor having two opposed deformable barbs capable of penetrating bone tissue. Preferably, the non-threaded suture anchor has a body constructed from a metal and barbs formed from a shape-memory material. Generally, the non-threaded suture anchor may have a length of less than about 4.0 mm and a diameter of less than about 1.5 mm. Preferably, the non-threaded suture anchor has a length of about 3.7 mm and a diameter of about 1.3 mm.

The pilot holes may be formed using a drill bit having an effective length of less than about 5 millimeters. The drill bit may also have a scoring means suitable to provide clearance around the pilot hole to allow for a suture anchor insertion tool to insert the microanchor at or below the surface of the cranium.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

The present invention concerns a procedure for supporting the soft tissue of a patient's scalp in a superior position using a suture anchor device. The patient is brought into an operating room where either general or intravenous sedation anesthesia is administered. The patient's face and scalp are cleansed with an antiseptic solution and draped under a sterile technique.

Figure 1:
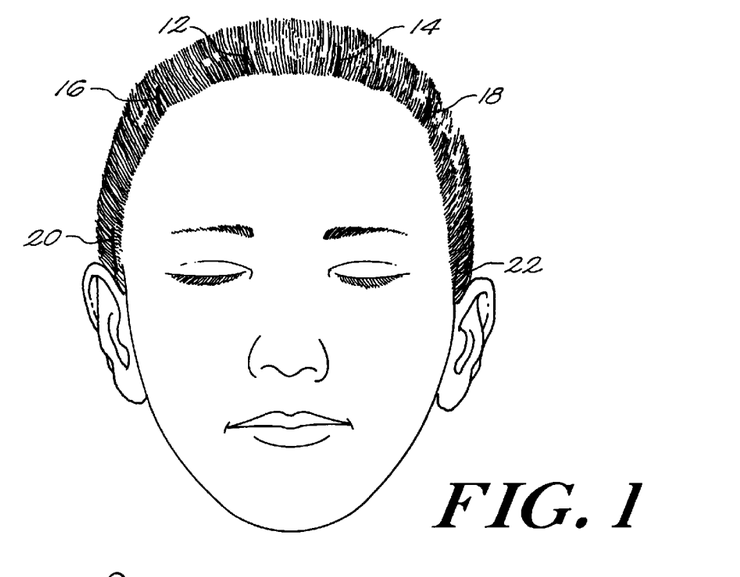
FIG. 1 is an elevated view of a patient's head indicating the location of incisions.

As shown in FIG. 1, two medial parasagital 12, 14 and two lateral 16, 18 brow incisions approximately 1 cm proximal to the hairline and 1.5 to 2.0 cm in length, are made and carried down to the periosteum. Bilateral temporal scalp incisions 20, 22 are made to allow access to the temporal parietal region. The temporal scalp incisions 20, 22 start approximately 1 cm above the root of the helix of the ear and extend superiorly 3 cm. Alternatively, five scalp incisions may be used instead of six, combining the two medial incisions 12, 14 into one central incision. The lateral scalp incisions 16, 18 may also be angled 30 degrees, providing more lateral eyebrow elevation and altering the eyebrow shape. The scalp incisions are infiltrated with a 1% lidocaine and 1:100,000 epinephrine solution. The remainder of the scalp is infiltrated with a dilute local anesthetic, according to the preference of the surgeon. One of ordinary skill in the art will appreciate that alternative incisions, varying in size and location from those noted above, may be effectively utilized without departing from the scope of the invention.

Figure 2:
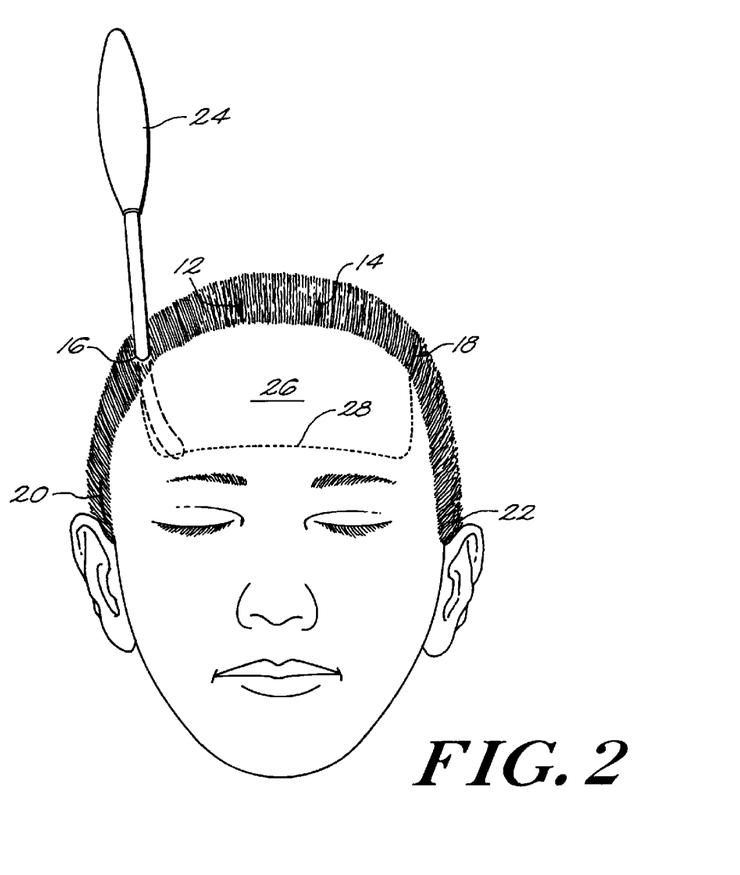
FIG. 2 is an elevated view of a patient's head showing a periosteal elevator in use undermining a portion of the patient's soft tissue.
Figure 3:
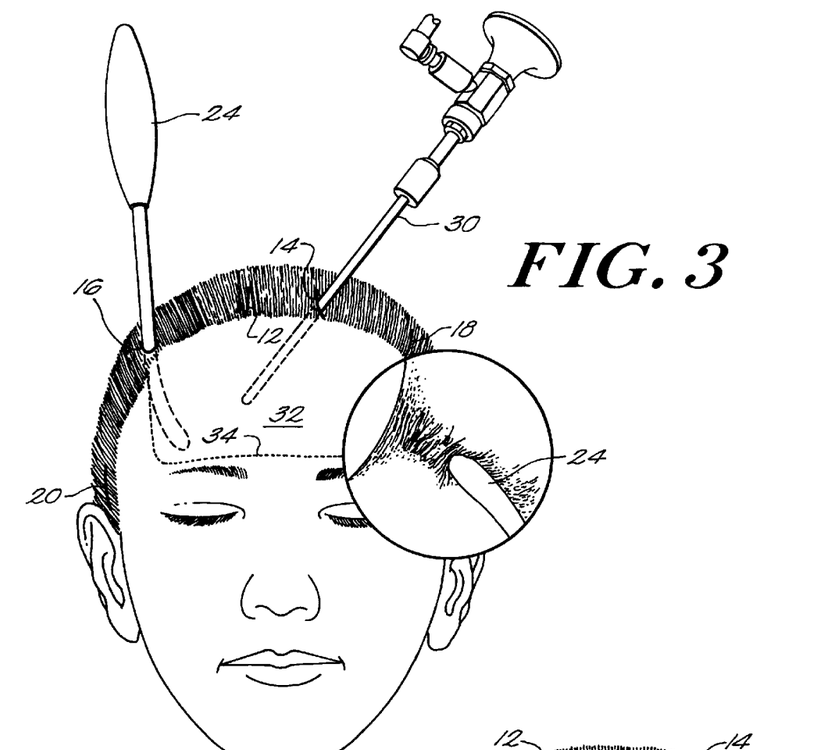
FIG. 3 is an elevated view of a patient's head showing a periosteal elevator and an endoscope in use with an insert illustrating a view through the endoscope.

A periosteal elevator 24 is used to undermine the scalp 26 anteriorly in a subperiosteal plane and posteriorly in a subgaleal plane as illustrated in FIG. 2. The anterior dissection may be performed blindly up to a line 28 approximately 2 cm above the level of the brow. As shown in FIG. 3, a 30 degree 4 mm endoscope 30 is introduced through a scalp incision, and under direct vision the remainder of the forehead 32 is undermined up to the level of the brow 34. The basic endoscopic brow instrumentation is similar to that used for various endoscopic and arthroscopic procedures, and numerous brow/mid-face endoscopic instrument sets are available to those of ordinary skill in the art. An exemplary endoscope is a 6 or 7 inch, 4 to 5 mm, 30 degree down viewing scope with a halogen light source. A protective sheath for the scope is also preferred.

Figure 4:
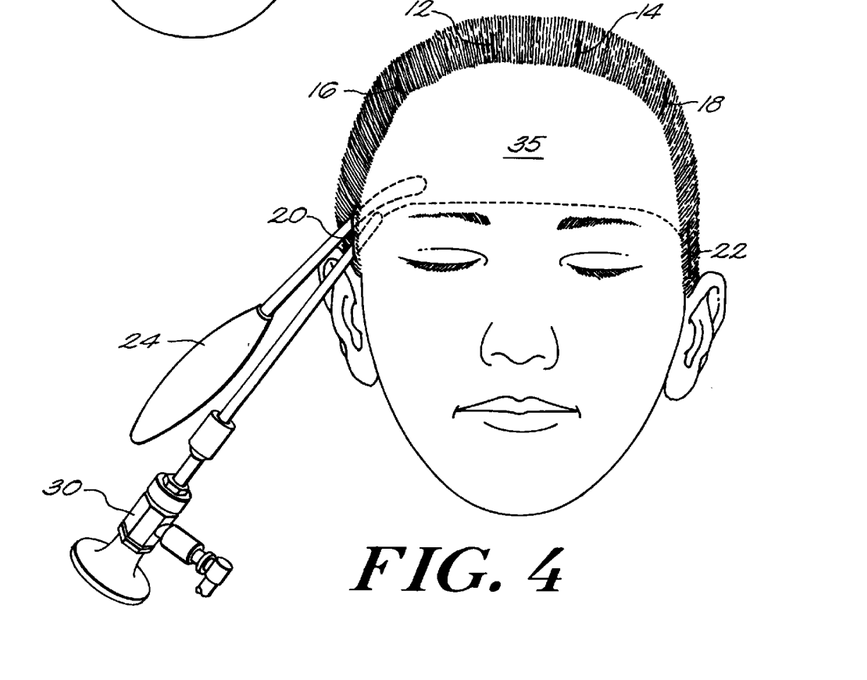
FIG. 4 is an elevated view of a patient's head showing a periosteal elevator and an endoscope in use through a temporal incision.

Next, as shown in FIG. 4, the dissection is carried out through the temporal incisions 20, 22 medially above the level of the common temporal fascia until the dissection meets with the subperiosteal dissection of the forehead. The frontal and temporal regions are then widely undermined creating a continuous frontotemporal flap 35. Through the same incision, the periosteum along the lateral orbital rim is elevated to the level of the lateral canthus.

Figure 5:
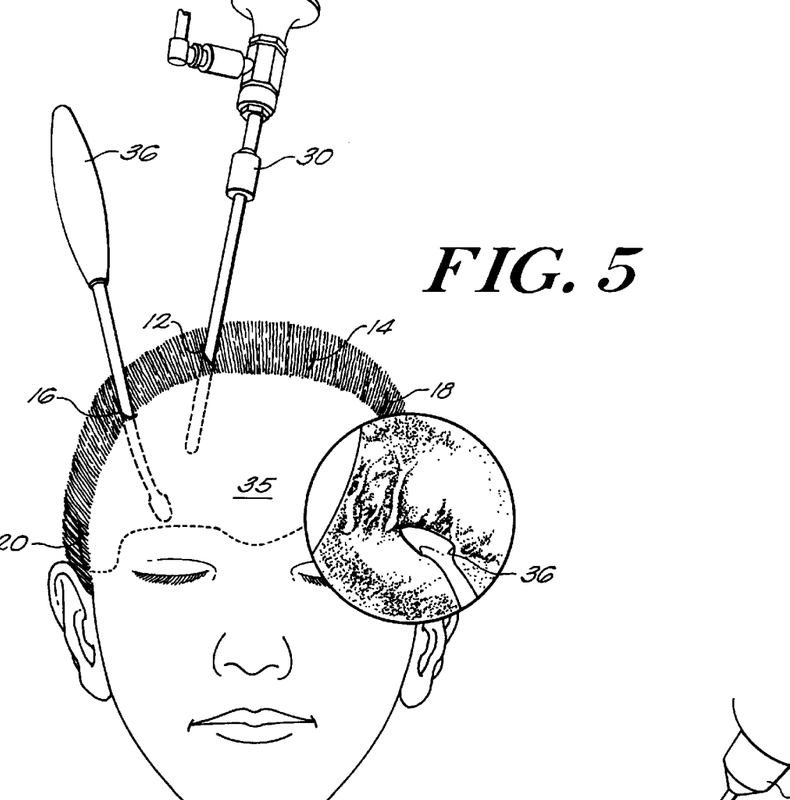
FIG. 5 is an elevated view of a patient's head showing a periosteal elevator and an endoscope in use with an insert illustrating a view through the endoscope.

The endoscope 30 is repositioned through a scalp incision, and the periosteum along the supraorbital rim is released by using a curved elevator 36 and a gentle upward sweeping motion as indicated in FIG. 5. A cautious and meticulous dissection is necessary to avoid injuring the underlying neurovascular structures. Hemostasis may be achieved with an electrocautery device as is known to one of ordinary skill in the art.

Figure 6:
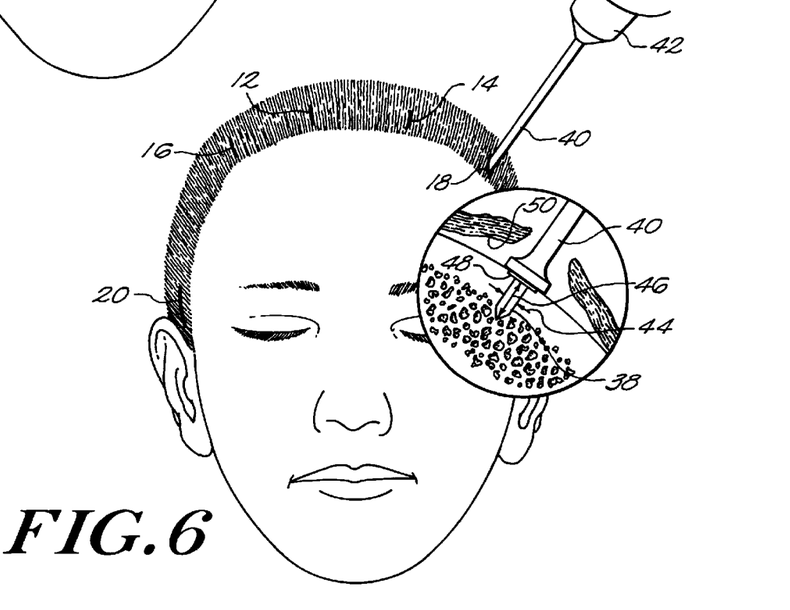
FIG. 6 is an elevated view of a patient's head showing a drill and drill bit being applied through an incision with a cross-sectional view in insert.

At this point, the brows can be moved and rigidly fixed into the desired superior position. As illustrated in FIG. 6, a single pilot hole 38 may be made through each of the frontal scalp incisions 12–18 using a drill bit 40 on a hand-held power drill 42. Generally, the drill bit 40 has a diameter 44 of less than 2.0 mm and a stop length 46 of less than 5.0 mm. In one embodiment, the drill bit has a diameter 44 of about 1.7 mm and a 4 mm stop length 46. The stop 48 on the drill is designed to score the outer cortex of the cranium to allow for a flatter profile of an anchor after insertion. The periosteum 50 surrounding the pilot hole 38 should be fully elevated before drilling begins. The pilot hole 38 is preferably drilled on the posterior edge of the incision after manually placing the forehead flap 35 on maximal tension. This allows for optimal adjustment of the tension of the forehead flap 35.

Next, one or more suture anchor devices, such as microanchors, are provided. The term "microanchor," as used herein, refers to a device for anchoring sutures within bone having a generally cylindrical body including a first bone contacting end, a second trailing end and bone fixation means formed on at least a portion of an outer surface of the microanchor between the first and second ends. The microanchor has a length of less than about 4.0 mm and has a predetermined length of suture thread attached thereto. Preferably, at least one suture needle is attached to the suture thread.

Generally, two types of microanchors are preferred for use with the method of the invention. One example of a suitable microanchor for use with the method of the invention is a threaded suture anchor 52 illustrated in FIGS. 7–8. The exemplary threaded suture anchor 52 is substantially cylindrical and has a proximal end 54, an apex-forming distal end 56 and a sidewall 58 disposed between the proximal 54 and distal 56 ends. The distal end 56 may be self-tapping, or it may simply form an apex which may be threaded into a bore preformed within a bone. The threaded suture anchor 52 used with the system of the invention generally has a major diameter 60 (measured at the widest point of the anchor) of less than about 2.4 mm. More preferably the major diameter 60 of the anchor 52 is about 2.0 mm. The length 62 of the threaded suture anchor 52 is preferably less than 4.0 mm and more preferably is about 3.5 mm.

Figure 7:
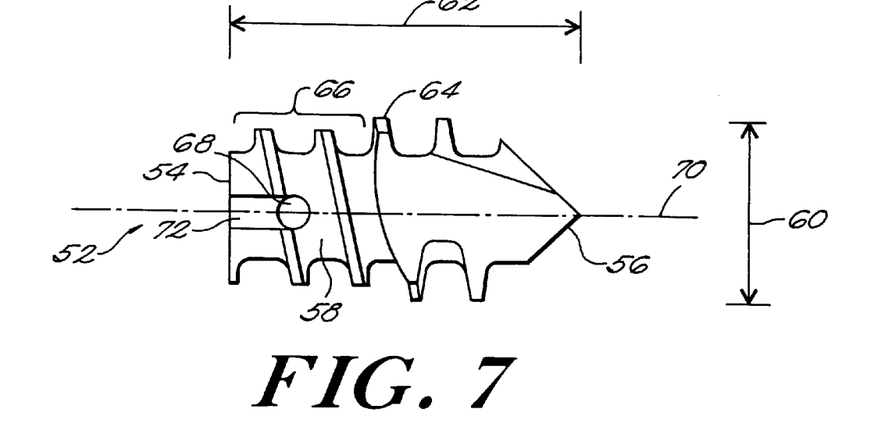
FIG. 7 is an elevated view of a threaded microanchor.
Figure 8:
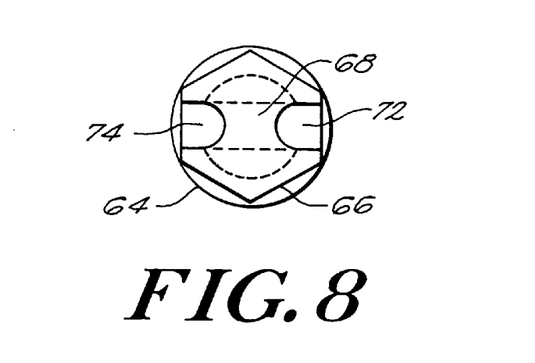
FIG. 8 is an end view of the threaded microanchor of FIG. 7.

The sidewall 58 of the threaded suture anchor 52 has at least one external thread 64 suitable for retaining the threaded suture anchor 52 within a bone. The shape of the proximal-most portion 66 of the threaded suture anchor 52 is configured to mate with a suture anchor inserting tool. In the exemplary threaded suture anchor 52, the proximal-most portion 66, including external threads on this portion, is in the form of a hexagon.

The threaded suture anchor 52 preferably includes a hole 68 that extends in a direction transverse to a longitudinal axis 70 of the anchor 52. The hole 68 is useful to seat a portion of suture thread when the anchor 52 is operatively attached to a suture anchor insertion tool. Longitudinal grooves 72, 74 preferably communicate with the hole 68 and extend proximally therefrom. Longitudinal grooves 72, 74 are useful to seat a length of suture thread, and should be of a sufficient width and depth to seat a length of suture thread while the suture anchor 52 is mated to a suture anchor inserting tool or engaged within a bore in a bone.

Figure 9:
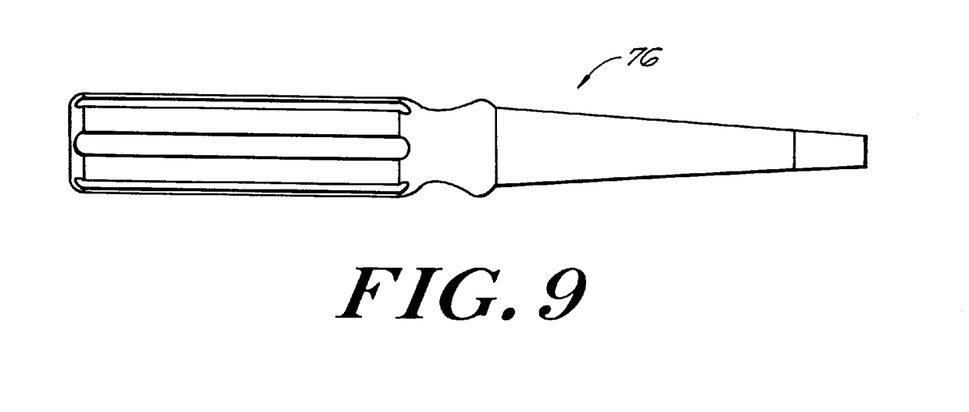
FIG. 9 is an elevated view of a suture anchor inserter for use with the threaded microanchor of FIG. 7.

An example of one threaded microanchor for use in the present invention is the Mitek® 2.0 mm Tacit™ Threaded Anchor available from Mitek Surgical Products, Inc. of Westwood, Mass. A suitable microanchor installation tool 76 (FIG. 9) for use with the threaded suture anchor is the Mitek® Tacit™ Inserter, also available from Mitek Surgical Products, Inc. Additional microanchor installation tools useful in the present invention will be readily apparent to one o ordinary skill in the art. One such tool is described in co-pending U.S. patent application Ser. No. 08/870,856, filed Jun. 6, 1997.

Figure 10:
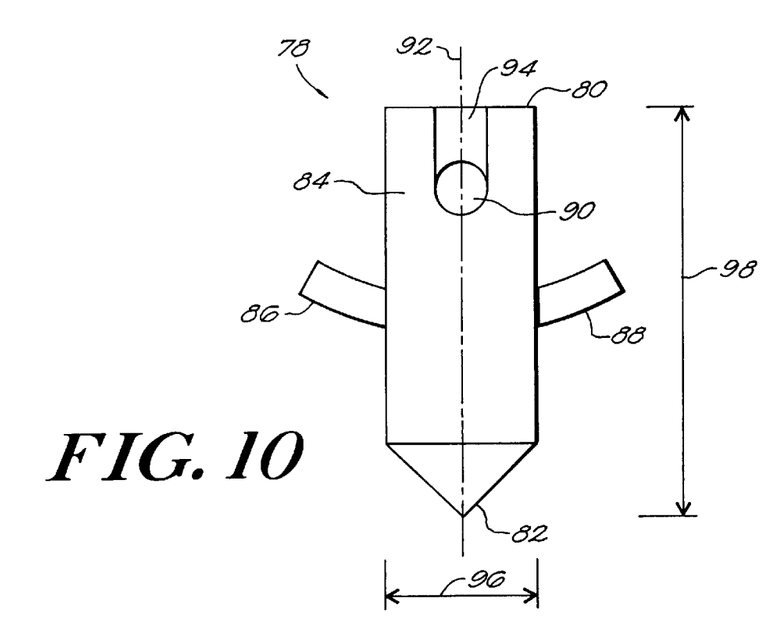
FIG. 10 is an elevated view of a non-threaded microanchor.

Alternatively, the microanchor provided in the present method may be a non-threaded suture anchor 78, illustrated in FIG. 10. The non-threaded suture anchor 78 includes a substantially cylindrical body with a proximal end 80, a distal end 82 forming an apex and a sidewall 84 disposed between the proximal 80 and distal 82 ends. The suture anchor 78 also has two opposed deformable barbs 86, 88 extending from the sidewall 84. The free ends of the deformable barbs 86, 88 may extend outwardly from the sidewall 84 and proximally (toward the proximal end 80 of the suture anchor 78) such that each barb defines an angle that is between about 10° and 90° with respect to the sidewall 84. More or fewer deformable barbs may be provided as desired to ensure proper retention of the suture anchor 78 within a bone. The non-threaded suture anchor 78 may be constructed from a metal such as titanium or a titanium alloy while the deformable barbs 86, 88 are preferably formed from a shape memory material such as nickel-titanium or NITINOL.

The suture anchor 78 further includes a hole 90 that extends in a direction that is transverse to a longitudinal axis 92 of anchor 78. The hole 90 is useful to seat and retain a portion of suture thread during insertion of the suture anchor 78 into bone. Longitudinal grooves 94 (only one of two shown), which are similar to grooves 72, 74 (FIGS. 7 and 8), are also provided on the suture anchor 78. These grooves 94 communicate with the hole 90 and extend proximally therefrom.

When non-threaded suture anchors are used with the system of the invention, such as the barbed suture anchor 78, the non-threaded suture anchor generally has a diameter 96 of less than about 1.5 mm. More preferably the diameter 96 of the non-threaded suture anchor 78 is about 1.3 mm. The length 98 of the non-threaded suture anchor 78 is typically less than 4.0 mm and more preferably is about 3.7 mm.

Figure 11:
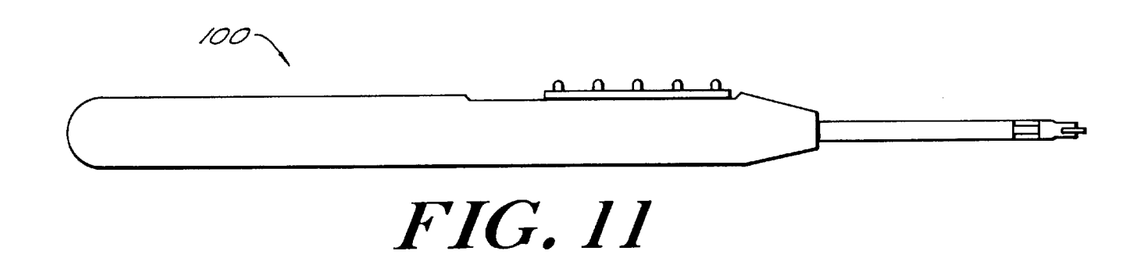
FIG. 11 is an elevated view of a suture anchor inserter for use with the threaded microanchor of FIG. 10.

An exemplary non-threaded microanchor for use in the present invention is the Mitek® 1.3 mm Micro Anchor available from Mitek Surgical Products, Inc. of Westwood, Mass. An exemplary microanchor installation tool 100 (FIG. 11) for use with the non-threaded suture anchor is disclosed in U.S. Pat. No. 5,662,658, which is hereby incorporated by reference. One of ordinary skill in the art will readily appreciate that other installation tools may be sued as well.

The microanchor is loaded with suture thread and placed on the end of an inserter. One of ordinary skill in the art will appreciate that suture thread may be constructed from a variety of suture materials. Exemplary materials include, but are not limited to, braided polyester and polydioxanone (PDS).

Figure 12:
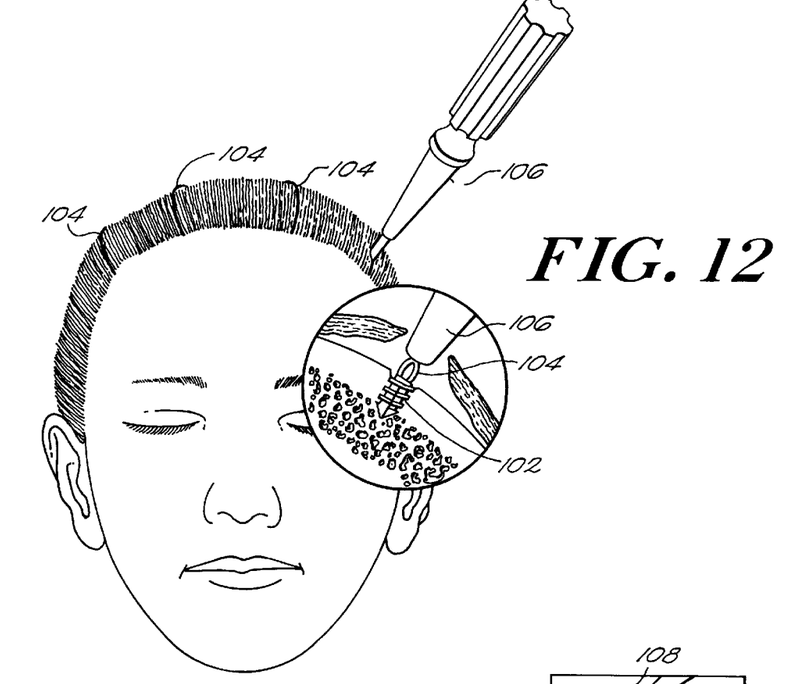
FIG. 12 is an elevated view of a patient's head showing a microanchor being inserted through an incision with a cross-sectional view in insert.
Figure 13:
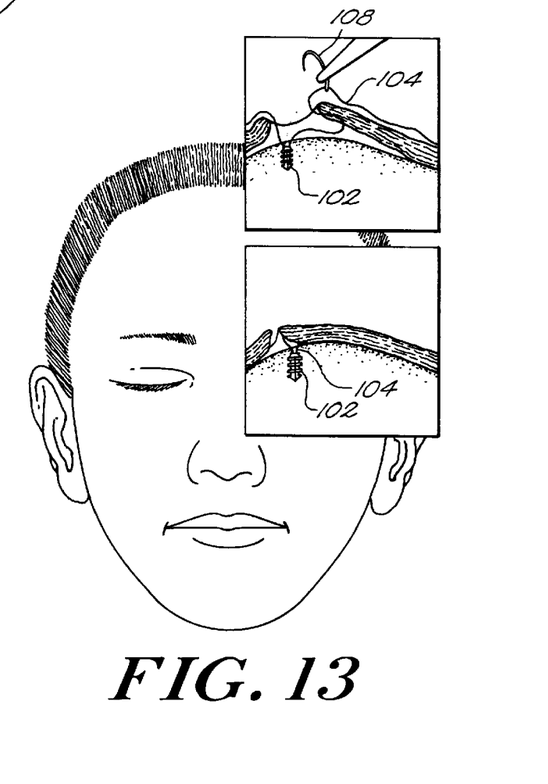
FIG. 13 is an elevated view of a patient's head illustrating the suturing of soft tissue in two inserts.

Once a microanchor 102 and suture thread 104 are properly seated on an inserter 106, a microanchor 102 is then inserted through each of the predrilled holes on the frontal bone, as shown in FIG. 12, by turning the inserter in a clockwise fashion until the microanchor 102 is seated at or below the surface of the cranium. Release of the suture anchor 102 will be automatic. The inserter 106 is removed, taking care not to dislodge the suture 104 from the anchor 102.

Where suture needles have not been preattached to the suture thread 104, a free end of the suture 104 is threaded through the eyelet of a French-eye needle 108 (FIG. 13). Starting on the anterior edge of the scalp incision, the suture 104 is passed through the subdermis, galea aponeurotica, and periosteum, taking a generous amount of the soft tissue. The sutures are tied under direct vision while carefully examining the brow for proper positioning. The sutures controlling the lateral brow position should be tied first since these hold the greatest amount of tension. An assistant should support the forehead flap to reduce tension and avoid breaking the suture. After tying all the sutures, a final check for symmetry is made. If needed, an ellipse of full thickness skin is excised from the temporal incision to control for skin laxity and lateral periorbital wrinkling (crow's feet).

To avoid alopecia, all wounds may be closed with a stapling device as known by one of ordinary skill in the art. The wounds are dressed with antibiotic ointment and a snug head dressing is applied. The patient is awakened from anesthesia and delivered to the recovery area. Prophylactic antibiotics and steroids are used according to each surgeon's discretion. The head dressing is removed after 24 hours and no further dressings are necessary. The staples may be removed on the 7th to 10th postoperative day, and the sutures remain in place.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A surgical procedure for supporting soft tissue of a patient's scalp in a superior position using a suture anchor, comprising the steps of:

making a plurality of incisions proximate to the soft tissue to be moved;

inserting an endoscope through at least one of the incisions;

undermining the soft tissue to be moved while viewing at least a portion of the undermining process through the endoscope;

forming at least one pilot hole in the cranium through one of the incisions;

providing one or more microanchors having a generally cylindrical body including a first bone contacting end, a second trailing end and bone fixation means formed on at least a portion of an outer surface of the microanchor between the first and second ends, the one or more microanchors each having a length of less than about 4.0 mm and having a predetermined length of suture thread attached thereto;

inserting the one or more microanchors into the at least one pilot hole in the cranium;

moving the soft tissue to a desired superior position; and suturing the soft tissue in the desired position.

2. The procedure of claim 1, wherein the bone fixation means comprise external threads with a major diameter of less than about 2.4 mm.

3. The procedure of claim 2, wherein the microanchor has a length of about 3.5 mm and a major diameter of about 2.0 mm.

4. The procedure of claim 2, wherein each microanchor is constructed from a metal.

5. The procedure of claim 1, wherein each microanchor is removably pre-mated to a suture anchor insertion tool.

6. The procedure of claim 1, wherein the bone fixation means comprises at least one deformable barb capable of penetrating bone tissue.

7. The procedure of claim 6, wherein the microanchor body is composed at least partially of titanium and the deformable barbs are constructed from a shape memory material.

8. The procedure of claim 7, wherein the bone fixation means comprises two opposed deformable barbs capable of penetrating bone tissue.

9. The procedure of claim 6, wherein the microanchor has a diameter of less than about 1.5 millimeters.

10. The procedure of claim 9, wherein the microanchor has a diameter of about 1.3 and a length of about 3.7 mm.

11. The procedure of claim 6, wherein each microanchor is removably pre-mated to a suture anchor insertion tool.

12. The procedure of claim 1, wherein the pilot holes are formed using a drill bit having an effective length of less than about 5 millimeters and having a scoring means suitable to provide clearance around the pilot hole to allow for a suture anchor insertion tool to insert the microanchor at or below the surface of the cranium.

13. The procedure of claim 1, wherein the plurality of incisions include parasagital incisions carried down to the periosteum, are located proximally to the hairline of the scalp and have a length between approximately 1.0 and 2.0 millimeters.

14. The procedure of claim 13, wherein a periosteal elevator is employed to undermine the tissue to be moved.

15. The procedure of claim 13, wherein pilot holes are drilled in a posterior portion of the incisions after manually placing the soft tissue in the desired position.

16. A surgical procedure for supporting soft tissue of a patient's scalp in a superior position using a suture anchor comprising:

making a plurality of incisions proximate to the hairline of the scalp;

undermining the soft tissue to be moved;

moving the soft tissue to a desired superior position;

providing at least one microanchor, pre-loaded with suture thread and removably pre-mated to a suture anchor insertion tool, the microanchor comprising a generally cylindrical body having external threads on at least a portion thereof, having a major diameter of less than about 3.0 millimeters;

forming a plurality of pilot holes in the scalp and corresponding cranium using a drill bit having an effective length of less than about 5 millimeters and having a scoring means suitable to provide clearance around the pilot hole to allow for a suture anchor insertion tool to insert the microanchor at or below the surface of the cranium;

inserting the microanchors into the pilot holes; and suturing the soft tissue into the desired superior position.

\* \* \* \* \*